US00PP08347P

United States Patent [19]

Vletter

[11] Patent Number: Plant 8,347

[45] Date of Patent: Aug. 17, 1993

[54] LILY PLANT NAMED ALASKA

[75] Inventor: Floris Vletter, Rijnsburg, Netherlands

[73] Assignee: Gebr. Vletter & J.A. den Haan, Rijnsburg, Netherlands

[21] Appl. No.: 796,694

[22] Filed: Nov. 21, 1991

[51] Int. Cl.[5] ..... A01H 5/00

[52] U.S. Cl. ..... Plt./87.4

[58] Field of Search ..... Plt./87.4

[56] References Cited

PUBLICATIONS

Leslie, A. C., 'Alaska' *The International Lily Register* 1982 The Royal Horticultural Society, London p. 5.

*Primary Examiner*—James R. Feyrer

*Attorney, Agent, or Firm*—Foley & Lardner

[57] ABSTRACT

A new and distinct cultivar of lily plant named Alaska, characterized by its brilliant white flower color with the base being a shade of light yellow, contrasting light brown pollen, dark purple-red spot markings on base, very small internodal length, and its strong stems.

1 Drawing Sheet

The present invention comprises a new and distinct cultivar of lily, botanically known as Lilium, known commercially as Lilium Asiatic hybrid, and hereinafter referred to by the cultivar name Alaska. The parents were asiatic varieties belonging to division I described in "Classification of Lily Cultivars into Divisions" published by Victoria Mathews, The Royal Botanic Gardens, Kew (1989).

The new cultivar is a product of a planned breeding program which had the objectives of creating new lily cultivars having white flower color, good forcing habits, and better disease resistance.

The new cultivar was originated from a hybridization made by the inventor in a controlled breeding program in Rijnsburg, The Netherlands in 1983. The female parent was an unnamed seedling, and the male parent was the cultivar Sancerre.

The new cultivar was discovered and selected as one flowering plant within the progeny of the stated cross by the inventor in June 1983 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary somewhat with variations in environment such as temperature, light intensity, and day length, without, however, varying the genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Brilliant white flower color, with the base or center being a shade of clear yellow;

2. Contrasting light brown pollen;
3. Dark purple-red spot marking;
4. Flowers are carried on strong stems;
5. Internodal length is very small thereby producing dense foliage.

Of the many commercial cultivars known to the present inventor, the most similar in comparison to the new cultivar is Apollo. In comparison to Apollo, Alaska has more flexible and stronger stems, spot markings on the flowers, and better disease resistance. When flowering is forced under natural light, Alaska produces an inflorescence approximately 44 days earlier than Stargazer, grown under the same conditions. Alaska is fertile.

The accompanying photographic drawing shows typical flower characteristics of the new cultivar, with colors being as true as possible with illustrations of this type. The photo is a top perspective view showing several flowers in full bloom and buds at varying stages.

In the following description, color references are made to The Royal Horticultural Society (R.H.S.) Colour Chart. The color values were determined at Wageningen in 1988–1989 and at Rijnsburg in July 1991.

Origin: Seedling from Breeding Program.

Parentage:

*Seed parent.*—Unnamed seedling.

*Pollen parent.*—Sancerre.

Classification:

*Botanical.*—Lilium.

*Commercial.*—Asiatic hybrid.

THE PLANT

Form: A single stem carrying numerous pedicels alternately arranged.

Height: Medium to tall, 90 cm at time of opening of anthers of first flower; when grown outside, approximately 50 cm.

Growth habit: Vigorous.

Stem: Angular in transverse section, internodal length 0.5 cm and uniform; color 145B; anthocyanin pigmentation present.

Foliage:

*Quantity.*—Approximately 60 leves, depending on growing conditions.

*Size of leaf.*—Mature leaves are short to medium in length, 7 cm; narrow in width, approximately 1.5 cm.

*Shape of leaves.*—Elliptical.

*Texture.*—smooth with strong glossiness upper side; no pubescence.

*Color.*—Medium green 137B.

Bulbs:

*Size.*—Outlet 6–22 cm.

*Color.*—White.

Roots: Both stem and contractile present.

THE BUD

Form: Tapering (like a lancet).

Size: 8 cm depending on growing conditions.

Opening: Unfolds normally.

Color: Light yellow (2D) color prior to opening.

Tepals: Folded, three visible.

THE FLOWER

Blooming habit: Raceme.

Size: Approximately 16 cm in diameter, depending on growing conditions.

Borne: Upright to horizontal.

Shape: Generally in form of hexagonal star.

Tepalage:

*Number of tepals.*—Six.

*Arrangement.*—Three inner and three outer.

*Color.*—Upper surface: White 155D.

Lower surface: White 155D; base and curvature near base yellow.

*Spotting or marking.*—Approximately 20 dark purple-red spot markings in center, each marking being approximately 0.5–1.0 mm in diameter.

Nectaries and papillae: Present.

Pedicel:

*Length.*—5 cm (length of pedicel of first flower).

*Color.*—Medium green with anthocyanin on the upper part.

Texture: Ribbed and papillose.

Disease resistance: No disease problems noted to date.

Fragrance: Absent.

Lasting quality: Excellent.

REPRODUCTIVE ORGANS

Stamens, anthers:

*Arrangement.*—Anthers form a generally circular pattern.

*Length.*—Very short (5.5 cm).

*Number.*—Six.

*Filaments.*—Yellow to light yellow.

Pollen color: Light brown.

Anther color: Purple.

Pistils: Short; one; green style; total length of pistil 6.5 cm.

Stigma: Purple stigma.

Ovaries: Triangular in shape other characteristics typical of asiatic lily varieties.

I claim:

1. A new and distinct cultivar of lily plant named Alaska, as illustrated and described.

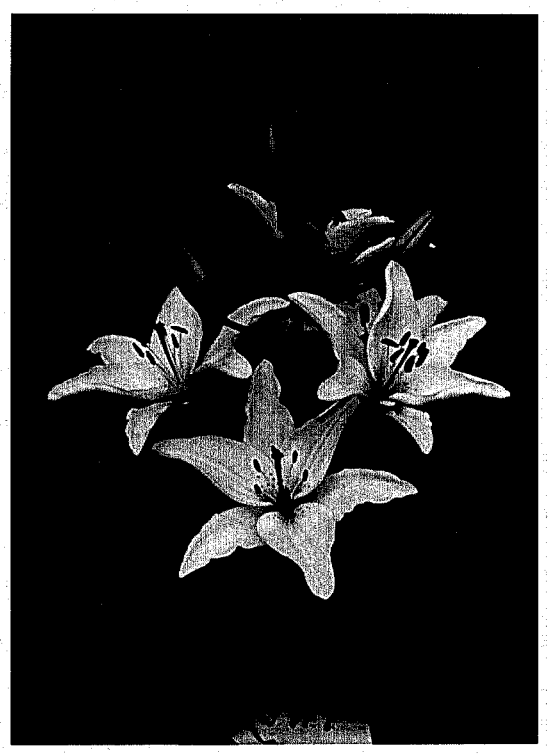

* * * * *